United States Patent [19]

Akins, Jr. et al.

[11] Patent Number: 5,275,708
[45] Date of Patent: Jan. 4, 1994

[54] CETYLTRIMETHYLAMMONIUM BROMIDE GEL ELECTROPHORESIS

[75] Inventors: Robert E. Akins, Jr., Ashford, Conn.; Rocky S. Tuan, Chester Springs, Pa.

[73] Assignee: Thomas Jefferson University, Philadelphia, Pa.

[21] Appl. No.: 853,963

[22] Filed: Mar. 20, 1992

[51] Int. Cl.$^5$ ............... G01N 27/26; G01N 27/447
[52] U.S. Cl. ........................ 204/182.8; 204/299 R
[58] Field of Search ........................................ 204/299

[56] References Cited

PUBLICATIONS

Shio Makino, Jacqueline A. Reynolds, and Charles Tanford "The Binding of Deoxycholate and Triton X—100 to Proteins" Journal of Biological Chemistry vol. 248 No. 14 (1973) pp. 4926–4932.
Maureen Melvin "Electrophores" pp. 36–39 (1987) John Wiley & Sons.
Shio Makino "Interaction of Proteins with Amphiphilic Substances" Adv. Biophys. vol. 12 (1973) pp. 131–184.
Anna G. Cavinato, Robert M. Mcleod, and Mahmoud S. Admed "A Non-Denaturing Gel Electrophoresis System for the Purification of Membrane Bound Proteins" Preparative Biochemistry, 18(2)(1988) pp. 205–216.
Shio Makino et al "Detection of the Associated State of Membrane Proteins by Polyacrylamide Gradient Gel Electrophoresis with Non–Denaturing Detergents" Biochimica et Biophysica Acta, 643 (1981) pp. 509–518.
Anthony T. Andrews *Electrophoresis; Theory, Techniques, and Biochemical Clinical Application*, 2nd ed. Chapter 5 "Polyacrylamide Gel Electrophoresis in the Presence of Detergents" pp. 117–118.
Leonard Ornstein "Disc Electrophoresis I, Background and Theory" Annals New York Academy of Sciences 121 (1964), pp. 321–349.
Dianne T. Akin, Raymond Shapira, and Joseph M. Kinkade, Jr. "The Determination of Molecular Weights of Biologically Active Proteins by Cetyltrimethylammonium Bromide-Polyacrylamide Gel Electrophoresis" Analytical Biochemistry, 145 (1985), 170–176.
U. K. Laemmli "Cleavage of Structural Proteins during the Assembly of the Head of Bacteriophage T$_4$" Nature vol. 227 (1970), pp. 680–685.
Akin et al., *Anal. Biochem.*, 145:170–176 (1985).

Davis, *Ann. NY Acad. Sci.*, 121:404–427 (1964).
Eley et al., *Anal. Biochem.*, 92:411–419 (1979).
Hearing et al., *Anal. Biochem*, 72:113–117 (1976).
Laemmli, U. K. *Nature*, 227:680–685 (1970).
Manrow and Dottin, *Proc. Natl. Acad. Sci.* USA, 77:730–734 (1980).
Marjanen and Ryrie, *Biochem Biophys. Acta.*, 37:442–450 (1974).
Nozaki et al., *J. Biol. Chem.*, 249:4452–4459 (1974).
Oakley et al., *Anal. Biochem.*, 105:361–363 (1980).
Ornstein, *Ann. NY Acad. Sci.*, 121:321–349 (1964).
Panyim et al., *Anal. Biochem.*, 81:320–327 (1977).
Polet and Steinhardt, *Biochemistry*, 7:1348–1356 (1968).
Ray et al., *Biochemistry*, 5:2606–2616 (1966).
Reynolds et al., *Biochemistry*, 6:937–947 (1967).
Scheele, *Clin. Chem.*, 28:1056–1061 (1982).
Schick, *Anal. Biochem.*, 63:345–349 (1975).
Shapiro et al., *Biochem, Biophys. Res. Commun.*, 28:815–820 (1967).
Spencer and Poole, *J. Mol. Biol.*, 11:314–326 (1965).
Tuan and Knowles, *J. Biol. Chem.*, 259:2754–2763 (1984).
Weber and Osborn, *J. Biol. Chem.*, 244:4406–4412 (1969).

*Primary Examiner*—John Niebling
*Assistant Examiner*—John S. Starsiak, Jr.
*Attorney, Agent, or Firm*—Woodcock Washburn Kurtz Mackiewicz & Norris

[57] ABSTRACT

A discontinuous polyacrylamide and agarose gel electrophoresis system is provided which allows the fine separation of proteins based on molecular weight with the concomitant retention of native enzymatic activity. This system, referred to as the CAT gel, uses the cationic detergent CTAB, and includes a stacking gel based on a zwitterion such as arginine and a buffer such as tricine. The CAT gel system allows specific enzyme histochemical detection and localization of proteins after gel electrophoresis. This system stacked and separated a broad range of proteins into discrete bands which migrate as a linear function of log $M_r$. The effect of CTAB solubilization on the activity of several proteins is also shown. Proteins separated by CAT electrophoresis maintain high levels of native enzymatic activity, and may be detected histochemically in situ.

8 Claims, 5 Drawing Sheets

CETYLTRIMETHYLAMMONIUM BROMIDE GEL ELECTROPHORESIS

BACKGROUND OF THE INVENTION

The electrophoretic separation of protein mixtures has been a standard biochemical procedure for a generation of researchers. The most commonly used protocol, described by Laemmli, U. K. *Nature*, 227:680-685 (1970) takes advantage of observations made by Shapiro et al., *Biochem, Biophys. Res. Commun.*, 28:815-820 (1967) and Weber and Osborn, *J. Biol. Chem.*, 244:4406-4412 (1969) which showed that an anionic detergent, sodium dodecylsulfate (SDS), could be used for the separation of most proteins based on $M_r$. Solubilization with SDS combined with a discontinuous polyacrylamide gel system, as originally described by Ornstein, *Ann. NY Acad. Sci.*, 121:321-349 (1964) and Davis, *Ann NY Acad. Sci.*, 121:404-427 (1964) allows the fine separation of dissociated proteins into discrete bands.

In the Laemmli system, SDS binding forms protein complexes that are nearly indistinguishable in an electric field. This is accomplished in two ways: SDS binds to most proteins in a constant ratio, 1.4 g of SDS per 1 g of protein, and imparts a constant charge to mass ratio to each protein so that their free mobilities are approximately equivalent; and SDS binding, in the presence of a reducing agent, causes a drastic structural change in the protein resulting in the formation of an SDS/protein complex shaped like a prolate ellipsoid with dimensions related to the $M_r$, of the native protein. Since shape and charge density characteristics for all proteins in SDS are similar, separation based on $M_r$ is accomplished by electrophoresis through a support matrix with specific pore sizes The matrix acts as a sieve with smaller complexes moving through more easily than larger ones and, therefore, migrating further in the gel.

The characteristics of SDS/protein complexes (i.e., denatured conformation, constant charge to mass binding, and uniform shape) makes SDS the detergent of choice for many electrophoretic procedures, especially those involving the identification of subunits or in analyses of sample purity. Many researchers have come to rely on SDS-PAGE for the convenient assignment of $M_r$ based on relative mobilities; however, it is difficult to assess the biological activity of proteins treated with SDS, although several proteins have been shown to renature to an active form after detergent removal, Manrow and Dottin, *Proc. Natl. Acad. Sci. USA*, 77:730-734 (1980) and Scheele, *Clin. Chem.*, 28:1056-1061 (1982). Another electrophoretic method, using the non-ionic detergent Tx-100, is commonly used in the production of zymograms, Hearing et al., *Anal. Biochem.*, 72:113-117 (1976), unfortunately, this technique does not separate proteins based on size and the assignment of $M_r$ requires multiple runs at different gel concentrations, Tuan and Knowles, *J. Biol. Chem.*, 259:2754-2763 (1984).

Akin et al. disclosed an entirely different electrophoretic system based on the cationic detergent CTAB that combines the most useful aspects of both the SDS and Tx-100 gels, Akin et al., *Anal. Biochem.*, 145:170-176 (1985). Previous reports of electrophoresis systems, based on CTAB and related detergents, clearly demonstrate the separation of proteins as a logarithmic function of their $M_r$, Eley et al., *Anal. Biochem.*, 92:411-419 (1979), Panyim et al., *Anal. Biochem.*, 81:320-327 (1977), Schick, *Anal. Biochem.*, 63:345-349 (1975), and Marjanen and Ryrie, *Biochem Biophys. Acta.*, 37:442-450 (1974). It has been shown that solubilization in CTAB does not cause loss of enzyme activity by denaturation, Spencer and Poole, *J. Mol. Biol.*, 11:314-326 (1965). The work of Akin et al. further suggests that some proteins may be separated in a CTAB gel system and still retain native activity. For these gels, sample preparation is done without boiling and without the addition of reducing agent. Virtually all proteins prepared in this manner still migrate as a function of log $M_r$; however, in this continuous gel system resolution is less than optimal due to the absence of a stacking gel.

SUMMARY OF THE INVENTION

The present invention provides a novel CTAB-based protein electrophoresis system that combines separation as a function of $M_r$, maintenance of biochemical activity, and the improved resolution provided by the inclusion of a stacking gel. This system is referred to as CAT gel electrophoresis because it is cationic in nature, and because in the preferred embodiment, CTAB is used as a solubilizing agent, arginine (a zwitterion with a basic pI) as a stacking agent, and tricine as a counterion and buffer. The CAT gel gives excellent separation of protein mixtures as tight, discrete bands, maintains native enzymatic activity in a number of sample proteins, and eliminates the extensive rinsing that was necessary to remove excess phosphate prior to phosphatase, ATPase, or calcium dependent assays in prior art systems.

A method of agarose or acrylamide electrophoresis is provided by which a charged, non-denaturing surfactant acts as a solubilizing agent for proteins. Useful surfactants include cetyltrimethylammonium, tetradecyltrimethylammonium, decylsulfate, octylsulfate and dodecylsulphonate. Surfactant binding imparts a constant charge to mass ratio among treated proteins, and forms protein complexes of uniform hydrodynamic shape. The selected surfactant is included in both sample and tank buffers. The electrophoretic method further utilizes a zwitterion such as arginine, lysine or glycine, which acts as a high mobility current carrier in the tank buffer, as an agent to accomplish protein stacking due to low zwitterion mobility in the conditions of the stacking gel, and as a high mobility current carrier in the separator gel to allow efficient migration of stacked proteins. The electrophoretic method further utilizes a buffer, such as Tricine, Hepes, MOPS or Tris, to maintain selected pH levels in the tank buffer, sample buffer, stacking gel, and separating gel, and to act as a counter ion for the carrying of current.

DESCRIPTION OF THE DRAWINGS

FIG. 1 is a photograph showing the electrophoretic separation of proteins in a CAT gel. Protein samples were prepared as described in the Examples section: Lane I, *E. coli* protein (50 μl, 5 mg/ml); Lane 2, 0.1 mg/ml $M_r$ marker protein mixture (50 μl, 0.1 mg/ml) containing glyceraldehyde-3-phosphate dehydrogenase (144 kDa), β-galactosidase (116 kDa) phosphorylase-B (97.4 kDa), bovine serum album in (66 kDa)1 ovalbumin (45 kDa), carbonic anhydrase (29 kDa), trypsinogen (24 kDa appearing as a 48 kDa dimer), soy bean trypsin inhibitor (20.1 kDa), and o-lactalbumin (14.2 kDa), the hash marks to the right side of the gel represent the position of these proteins; Lane 3, chick chorioallantoic membrane (CAM) microsomal membrane proteins (200 μl, 1.5 mg/ml); Lane 4, horseradish peroxidase (HRP) (200 μl, 0.1 mg/ml). Electrophoresis was carried out in the Hoefer Sturdier apparatus at 100 V through a 4% T acrylamide stacker and 150 V through an 8% T acrylamide separator. The gel was stained with Coomassie Blue (CBS) and photographed to show protein separation and band resolution.

FIG. 2 is a graphical depiction of protein electrophoretic mobility as a function of $M_r$ in a CAT gel. Mixtures of standard proteins of known $M_r$ were prepared as described in the Examples section. The samples were heated to 100° C. in the presence of β-mercaptoethanol, to reduce and dissociate protein complexes, and then electrophoretically fractionated in a 6% T CAT gel with a 0.7% agarose stacker.

The proteins were stained with Coomassie Blue and $R_f$s calculated as distance migrated divided by distance to the salt front. These values were plotted against values of expected log $M_r$s. Multiple points at the same log $M_r$ represent the same protein as it appeared in various protein mixtures run in different lanes. The plot is linear ($R^2 > 0.99$) across the entire range. Proteins included in this figure: trypsinogen (24 kDa); carbonic anhydrase (29 kDa); glyceraldehyde-3-phosphate dehydrogenase (36 kDa); ovalbumin (45, 90 kDa); bovine serum albumin (66, 132, 198, 264 kDa); phosphorylase-B (97.4 kDa); β-galactosidase (116 kDa).

FIG. 3 is a graph showing a comparison of protein mobilities in CAT and Laemmli-SDS gels. Mixtures of proteins (myosin, 205 kDa; β-galactosidase, 116 kDa; phosphorylase-B, 97.4 kDa; bovine serum albumin, 66 kDa; ovalbumin, 45 kDa; carbonic anhydrase, 29 kDa) were prepared as described in the Examples section, and run on either a 6% T CAT-PAGE with a 4% T stacker or an 8% T SDS-PAGE with a 4% T stacker. The gels were stained with Coomassie Blue and log $M_r$ was plotted as a function of $R_f$.

FIG. 4 is a graphical depiction of the effect of detergent solubilization on enzyme activities. Enzyme activities were determined in the presence of 0.5% Tx-100, SDS, or CTAB as described in the Examples. The activities were expressed relative to that in Tx-100 solubilized samples (100%). Most proteins exhibited significantly higher activity in CTAB than in SDS. Alkaline phosphatase and horseradish peroxidase were purchased from Sigma. $Ca^{2+}$-ATPase activity was measured in microsomes prepared from day-17 chick chorioallantoic membrane, Oakley et al., Anal. Biochem., 105:361-363 (1980). NAD dependent isocitrate dehydrogenase (ICD) and lactate dehydrogenase (LDH) activities were measured in detergent extracts of JEG-3 human choriocarcinoma cells FIG. 5 is a photograph showing histochemical staining of enzyme activities in CAT gels. Two separate gels were prepared and histochemically stained to detect enzymes with representative banding patterns. Lane 1: 15 μl of 2 mg/ml chick CAM extract prepared in CAT sample buffer was loaded onto a 6% T CAT gel with a 0.7% agarose stacker. After electrophoresis at 4° C., the gel was stained for $Ca^{2+}$-ATPase activity and subsequently with Coomassie Blue for total protein (see FIG. 1, lane 3). Analysis of the $R_f$ value for the single activity band indicates an $M_r$ in close agreement to the published 170 kDa $M_r$, Tuan and Knowles, J. Biol. Chem., 259:2754-2763 (1984). Lane 2: 50 μl of 1 mg/ml HRP in CAT sample buffer was loaded onto a 6% T CAT gel with a 0.7% agarose stacker. After electrophoresis at room temperature, the gel was stained for horseradish peroxidase activity, and subsequently stained with Coomassie Blue to detect other protein bands (see FIG. 1, lane 4). Analysis of the $R_f$ values obtained for each activity band indicated that the activity bands correspond to dimeric (113 kDa) and trimeric (142 kDa) forms of the expected 45-50 kDa monomer detected by CBB staining.

DETAILED DESCRIPTION OF THE INVENTION

The electrophoretic separation of proteins is a powerful biochemical tool. The method presented here efficiently stacks and separates a wide range of proteins as a function of $M_r$ and preserves native enzymatic activity to such a degree that it should be applicable to the identification of proteins by both $M_r$ and enzymatic activity in a single gel. This method has proven especially useful when applied in conjunction with chromatographic fractionations, since the eluted fractions may be simultaneously characterized with respect to protein $M_r$ distribution and activity profile, and should provide a useful adjunct to other protocols currently in use.

CTAB is a cationic detergent, and when bound to proteins imparts a positive charge on them. Therefore, proteins run on CTAB gels migrate in the opposite direction compared to SDS gels, and the components of the electrophoresis system of the invention were chosen to accommodate this charge difference. For the system to run near pH 7.0, a zwitterion with a basic pI was sought for use as the low mobility ion in protein stacking. Two possibilities were investigated because of the availability of free base forms and their relatively low cost: arginine (pI ≈ 10.8) was found to be preferred to lysine (pI ≈ 9.74). Electrophoresis systems devised from either amino acid effected separation by $M_r$ (see FIG. 1 for arginine; data for lysine not shown), but protein bands in CTAB-lysine gels were generally more diffuse than those in CTAB-arginine gels. We attribute this to the fact that the α-NH₂ group of lysine ($pK_a \approx 9.06$) would tend to buffer near the pH needed for adequate stacking. In the lysine gels, therefore, the transitions from running buffer to stacking gel and from stacking gel to separating gel were less distinct and resulted in only nominal stacking and diffuse banding patterns. The remaining conditions of the system were predicated, in part, by the selection of arginine as the cationic stacking agent.

To allow efficient cathodic protein migration and stacking, tricine buffer was selected based on two fundamental criteria: a negative charge in solution to act as a counter ion for arginine, and a $pK_a$ near the pH of the separating gel and tank buffer (≈ 8.0 for an arginine based system). One drawback we have noted with the tricine buffer system is a slight increase in the time required for acrylamide polymerization in its presence at pH 8.0. Such inhibition was not seen if tricine was replaced by other buffers, e.g., HEPES or MOPS, but these buffers were less effective in maintaining pH during electrophoresis due to limited buffering capacities and apparent electrolytic degradation. Finally, crystal violet was selected as a tracking dye because it did not interfere with their gels or with the activities of the proteins they assayed.

The specifics for the selection of buffer and zwitterion concentrations in the CTAB discontinuous gel would have required calculations involving terms for tricine and arginine mobility. Since tris and tricine are structurally similar, we expected that tricine would have only a slightly lower mobility in the opposite direction to tris by virtue of its slightly higher $M_r$. The buffer concentrations used in the Laemmli SDS-PAGE system for gel formation were, therefore, expected to give similar performance in CAT gels. The gels described here gave excellent results, and no further modification of buffer concentrations was attempted. The concentrations of buffer and zwitterion in the tank buffer are not critical and were selected empirically based on the buffer capacity, conductivity, and solution density necessary to maintain pH, reduce heating, and facilitate gel loading.

CAT gels were run at either 25° or 4° C.; however, samples were always prepared at 25° C. immediately before running the gel. This was necessary because at the CTAB concentration used in the sample buffer, precipitation occurred at temperatures below 10°-15° C. The inclusion of protease inhibitors, when possible, is recommended as the elevated temperature necessary to maintain sample fluidity may, in some cases, compromise enzymatic activity because of the action of endogenous proteases. Finally, it should be noted that the accumulation of reactive $Br_2$ at the anode, caused by the electrolysis of CTAB during electrophoresis, may preclude the re-use of tank buffer.

Figure 1:
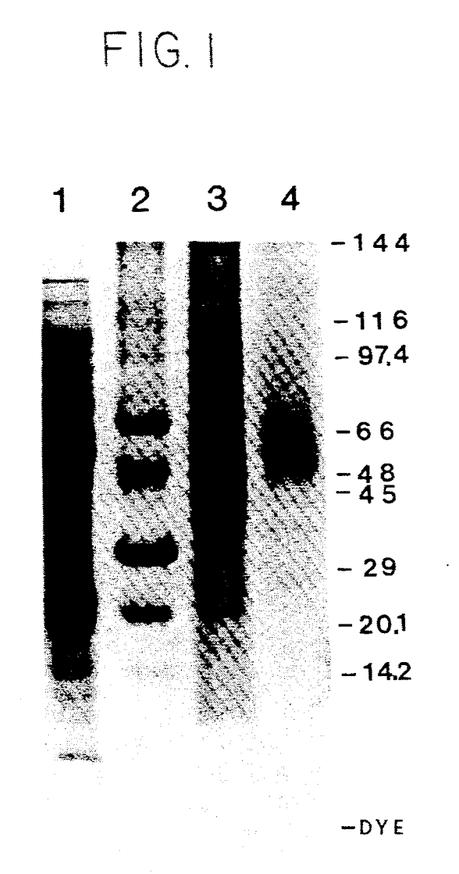
Figure 5:
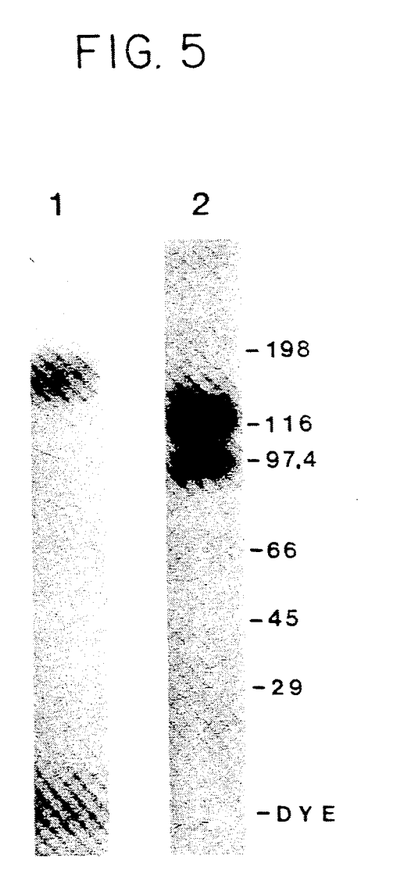

In general, proteins separated on CAT gels migrate in a manner similar to SDS-based gels. FIG. 1 shows several typical CAT gel electrophoretograms. The separation of proteins from solubilized (shown in lane 1) is typical of protein mixtures; however, in samples containing high levels of membrane lipid a more typical pattern is seen in the chick CAM preparation in lane 3. The primary lipid component of the CAM preparation is lecithin which may directly affect the interaction of CTAB with protein through both hydrophobic and ionic interactions. The standard proteins shown in lane 2 are those generally used as $M_r$ marker in SDS-based gels. Differences between the electrophoretic pattern seen in the CAT gel and that expected on an SDS gel are attributable to denaturation state: for example, glyceraldehyde-3-phosphate dehydrogenase appears as a 36 kDa band in SDS gels but as a 144 kDa native tetramer near the top of this CAT gel. These results are entirely consistent with the maintenance of enzymatic activity seen in CAT gels. HRP (in lane 4) appears to run as a single protein slightly above its expected 40-45 kDa $M_r$, the enzyme histogram of this preparation and the chick CAM preparation, as shown in FIG. 5, are discussed below.

The results show that the solubilization of some proteins with the cationic detergent CTAB does not cause complete loss of native enzymatic activity. AP, HRP, and ICD enzymes all exhibit relatively high levels of enzyme activity in CTAB compared to SDS. The plasma membrane $Ca^{2+}$-ATPase tested is sensitive to extensive solubilization of lipid components by several detergents, including Tx-100, often resulting in the loss of activity. The results for the integral membrane $Ca^{2+}$-ATPase in CTAB may thus reflect differences in membrane solubilization between CTAB and Tx-100, and not CTAB mediated protein denaturation. Similarly, the lack of activity for LDH may be a result of enzyme complex dissociation as opposed to a failure to maintain native secondary protein conformation.

Our gel histochemical analyses indicate that two different types of histograms may be produced by CAT electrophoresis. In the case of $Ca^{2+}$-ATPase, a single, histochemically stained band was seen at the appropriate $M_r$. This is consistent with previous observations of the histochemical staining of myeloperoxidase, esterase, and acid phosphatase, as well as detection of polynucleotide phosphorylase in CTAB based gels. HRP, on the other hand, displayed a more complex staining pattern: activity bands were seen at higher $M_r$ than expected for HRP monomer (see FIG. 1). It is not clear from our experiments whether the observed histochemical banding pattern of HRP is a result of differential CTAB binding (possibly due to the presence of hemin or to variable binding by HRP isoenzymes), or if the effect is simply due to the loss of activity in HRP monomer but not in HRP configured as multimers. Nevertheless, the appearance of an identifiable histochemical banding pattern for HRP would act as a "fingerprint", and could be used to ascertain the presence of the enzyme in a given sample.

The maintenance of native activity in CTAB has been previously attributed to the low critical micelle concentration (CMC) of CTAB and related detergents. A low CMC would preclude detergent-mediated denaturation of protein since the free detergent concentration required for denaturation would not be reached due to micelle formation. This is a possible explanation for the observation that certain proteins solubilized in excess CTAB retain enzymatic activity; however, it stops short of explaining the observed hydrodynamic result that proteins migrate as a function of $M_r$ at levels of bound detergent insufficient to cause massive denaturation.

Detergents, including SDS, bind to proteins in three distinct stages: low concentration, native binding; cooperative, non-denaturing binding, which occurs as the detergent monomer concentration increases; cooperative binding with massive denaturation. Cooperative, non-denaturative binding of 0.4 g SDS per 1.0 g protein occurs at free SDS concentrations below those used in the Laemmli system, and results in the formation of complexes with constant charge to mass ratios. Stable, cooperative binding apparently predominates for several non-denaturing, ionic detergents, Nozaki et al., *J. Biol. Chem.*, 249:4452-4459 (1974), Polet and Steinhardt, *Biochemistry*, 7:1348-1356 (1967), Reynolds et al., *Biochemistry*, 6:937-947 (1967), and Ray et al., *Biochemistry*, 5:2606-2616 (1966). A similar type of detergent condensation may be responsible for the generation of uniform charge to mass ratios among CTAB treated proteins, a criterion necessary for $M_r$-based separation by CTAB electrophoresis.

Figure 2:
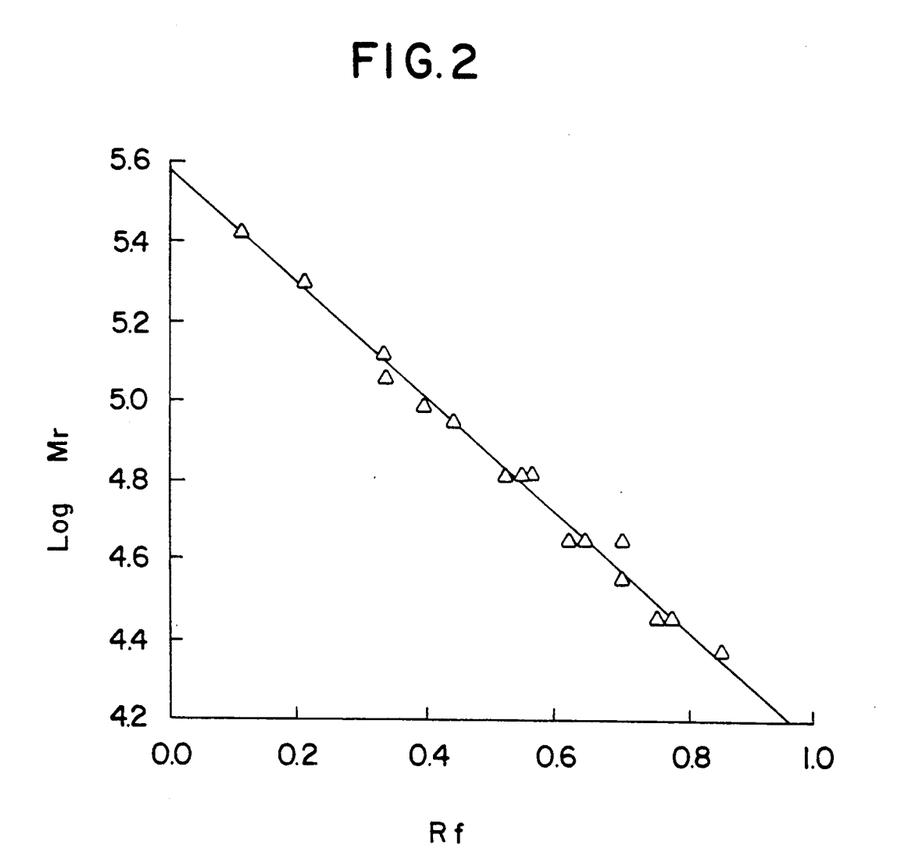
Figure 3:
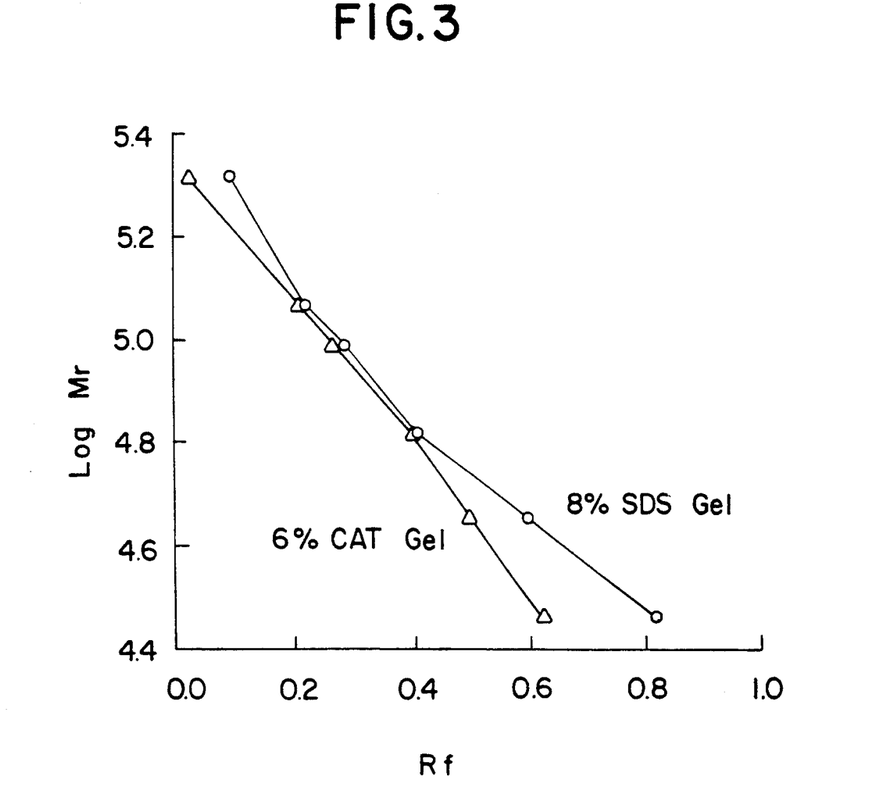

Another requirement for the electrophoretic separation of proteins based on log $M_r$ is a consistent hydrodynamic shape. Standard curves of log as a function of $R_f$ generated from CTAB gels display more extended linearity than similar plots generated using SDS gels (FIG. 3). This property indicates that either CTAB/protein complexes have a different shape than the rod shape attributed to SDS/protein formations, or that there are differences in the hydrodynamic sieving interactions between protein/detergent complexes and the polyacrylamide matrix found in the CAT system as opposed to the Laemmli system. Second, it was found that the $R_f$s of proteins fractionated by CAT electrophoresis are consistently lower than $R_f$s determined on the same % T SDS-PAGE. This phenomenon is possibly related to the larger $M_r$ and aggregation number of CTAB compared to SDS (365 Da and 170 monomers per micelle for CTAB versus 289 Da and 62 monomers per micelle for SDS), and it suggests that hydrodynamic differences between the detergents are not to be unexpected. The use of a 4% T acrylamide stacker (as in FIG. 3) led to the determination of $R_f$ values that are internally consistent but uniformly lower than those determined in an identical gel with a 0.7% agarose stacker (as in FIG. 2). This is most likely due to a sieving action by the stacker; agarose (or a mixture of agarose and polyacrylamide) gels may be useful especially when trying to separate high $M_r$ proteins.

CAT gels made of 8% T acrylamide, with a 4% T stacker, were loaded with protein mixtures in CAT sample buffer. Protein stacking was evaluated visually by Coomassie Blue staining. As shown in FIG. 1, efficient stacking was achieved using the CAT gel, and the separated proteins formed discrete bands, even when relatively large volumes of sample buffer were used in loading. The samples shown in FIG. 1 represent different types of protein preparations, including total E. coli. proteins (lane 1) and microsomal membrane proteins (lane 3).

Previous workers have shown that proteins fractionated on CTAB-based continuous gels, using various buffer conditions, yielded electrophoretic mobilities inversely proportional to log $M_r$. The degree to which the discontinuous CAT system with an arginine based stacking gel and an agarose stacker, affected $M_r$ based migration was assessed for the method of the invention. Mixtures of standard proteins were subjected to electrophoresis on 6% T polyacrylamide gels, with 0 7% agarose stackers. A typical plot of log $M_r$ versus $R_f$ is shown in FIG. 2. The results indicate that, for a wide range of proteins, $R_f$ is a logarithmic function of $M_r$.

During $R_f$ analysis of standard proteins run in the CAT system, it was noticed that protein mobility was apparently lower in CAT gels than in Laemmli-SDS gels of the same acrylamide composition. In order to directly compare relative differences in protein migrations in CTAB versus SDS, CAT gels of various concentrations were run and compared to a standard Laemmli-SDS gel. FIG. 3 shows the relative mobilities for a group of proteins in a 6% T CAT gel and an 8% T SDS gel; both gels were poured with 4% T acrylamide stackers for consistency. The two gel systems give similar protein profiles; however, the CAT gel showed extended linearity of the log $M_r$ vs. $R_f$ over a broader range of proteins. In addition, the $R_f$ analysis of this 6% T CAT gel with a 4% T acrylamide stacker showed increased retardation of proteins compared to the 6% T CAT gel with agarose stacker shown in FIG. 2.

Figure 4:
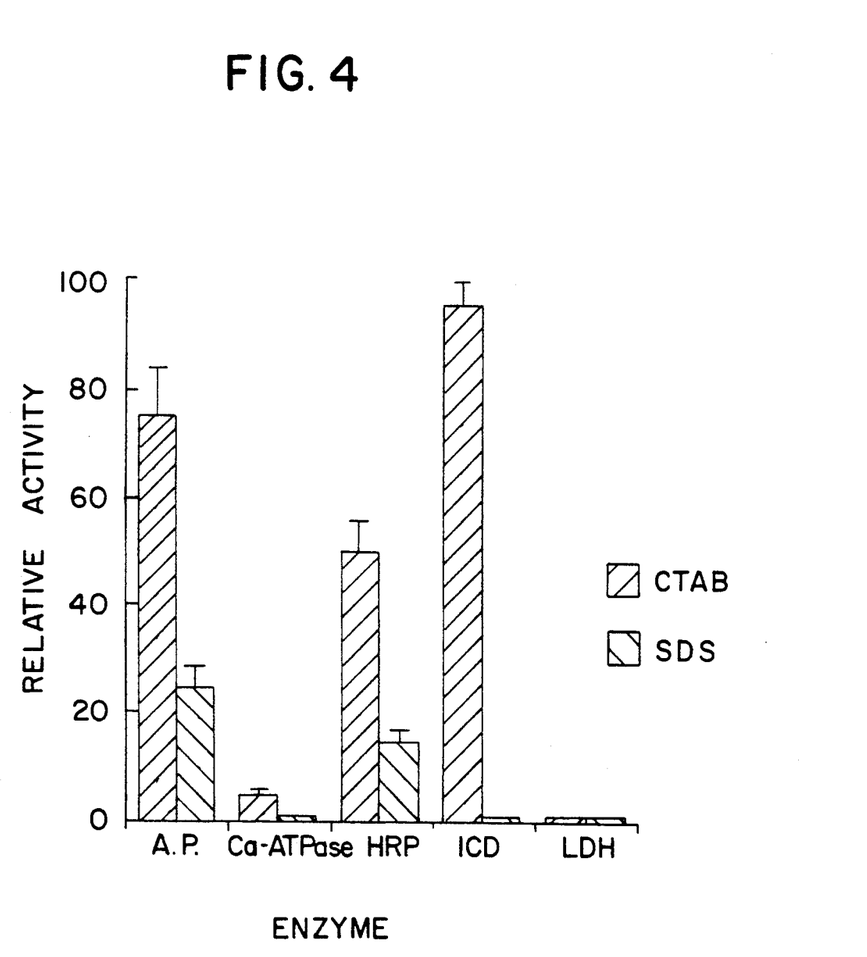

Native protein activity was retained after solubilization in CTAB. Enzyme activities of various proteins in CTAB with their activities when solubilized in SDS, or Tx-100 were compared. The results, shown in FIG. 4, indicate that although the CTAB buffer significantly affected all enzyme activities, particularly the transmembranous $Ca^{2+}-$ ATPase and the multi-subunit LDH, the treatment was considerably less deleterious than with SDS. CTAB or SDS treated samples that were heated to 100° C. in the presence of β-mercaptoethanol lost all activity, indicating that temperature is critical in the maintenance of native activity in the presence of these detergents. The relative effect of detergent solubilization on native activity varied from protein to protein and, therefore, must be determined empirically.

Previous reports utilizing continuous gel systems have indicated that enzymes maintain detectable levels of activity after CTAB based electrophoresis. FIG. 5 shows histochemical staining of $Ca^{2+}$-ATPase and HRP enzyme activities after these proteins were fractionated in 6% T CAT 35 gels with 0.7% agarose stackers. $Ca^{2+}$-ATPase activity was localized as a single band near the 170 kDa $M_r$. The HRP activity, on the other hand, corresponded to multiples of the known monomer $M_r$. Peroxidase activity in this HRP preparation was most prominent in bands representing trimeric and tetrameric forms; however, there was little or no activity in monomeric forms, though a protein band was clearly seen after CBB staining of the sample (see FIG. 1, lane 4).

The CAT system allows the simple determination of $M_r$ for active enzymes and should prove valuable in many situations. The CAT system may prove useful in the separation and isolation of polypeptides based on $M_r$, and for use in immunotechniques.

In general, the characteristics of CTAB/protein complexes may be useful criteria for the selection of other detergents for the preparation of alternate electrophoresis systems to accomplish the separation of enzymatically active proteins based on log $M_r$. The utility of CTAB in the CAT system is likely to be due to the formation of CTAB/protein complexes via the cooperative, non-denaturative binding of CTAB. Such binding may result in complexes with the following characteristics: maintenance of enzymatic activity; constant charge to mass ratio among complexes containing different proteins; and consistent hydrodynamic shape among complexes containing different proteins. Other detergents may be similarly useful if detergent binding results in complexes with similar characteristics. Alternative detergents must be selected from available "charged, non-denaturing surfactants", and may be chosen based on binding characteristics similar to CTAB. Previous workers have investigated the binding of some charged, non-denaturing surfactants in detail. From among these, several may be selected for use in a cationic system (like the CAT system) or an anionic system (like the Laemmli system). For example, positively charged (cationic) surfactants for use in an arginine/Tricine based system include cetyltrimethylammonium and n-tetradecyltrimethylammonium (Nozaki et al., *J. Biol. Chem.*, 249:4452-4459 (1974)). Other quaternary ammonium based detergents may also be useful. Negatively charged (anionic) surfactants for use in a glycine/Tris system include decylsulphate, octylsulphate and dodcylsulphonate (Ray et al., *Biochemistry*, 5:2606-2616 (1966); Reynolds et al., *Biochemistry*, 6:937-947 (1967); and Polet and Steinhardt, *Biochemistry*, 7:1348-1356 (1968)).

The invention is further illustrated by the following, non-limiting examples.

EXAMPLES

Example 1

Reagents and Supplies

Materials and their commercial sources include: acetic acid (Fisher Scientific, Pittsburgh, Pa.); acrylamide and bis-acrylamide (Amresco, Solon, Ohio); agarose (Fisher); arginine free base (Sigma Chemical Co., St. Louis, Mo.); ammonium persulfate (Sigma); crystal violet (Sigma); CBB (Fisher); CTAB (Sigma); enzyme diagnostic kits: alkaline phosphatase kit #245-10, lactate dehydrogenase diagnostic kit #228-10, and isocitrate dehydrogenase diagnostic kit #176-C (Sigma); diaminobenzidine (Sigma); glycerol (Sigma); hydrogen peroxide (Fisher); isopropanol (Fisher); methanol (Fisher); MiniProtean II gel apparatus (Bio-Rad Laboratories, Richmond, CA); protein standards (Sigma); sodium hydroxide (VWR Scientific, Media, Pa.); sodium sulfide (Fisher); Sturdier Gel apparatus (Hoefer Scientific Instruments, San Francisco, CA); TEMED (Sigma); tricine (Research Organics, Inc. Cleveland, Ohio).

Example 2

Sample Preparation

Protein samples were dissolved at room temperature to the indicated concentrations using a CTAB sample buffer which consisted of 10 mM tricine brought to pH 8.8 with NaOH, 1% CTAB, and 10% glycerol. In some instances, a saturated aqueous solution of crystal violet was added (10 μl/ml of CTAB sample buffer) to facilitate visualization of the salt front during electrophoresis. Samples for SDS gels were prepared after the method of Laemmli, *Nature*, 227:680-685 (1970).

Example 3

Casting and Running of CAT Polyacrylamide Gels

Separating gels were prepared from an ultra-pure stock solution of 40% T (w/v) with 2.67% C (w/w) of the acrylamide in the bis-acrylamide form. The stock was diluted at room temperature to the final concentrations indicated in the text (typically 6% T) with tricine-NaOH (pH 8.0) to a final concentration of 375 mM. Polymerization was initiated with 0.1 ammonium persulfate and 0.01% TEMED. Polymerization was allowed to proceed for at least 60 minutes to assure complete crosslinking, and stacking gels were made of 0.7% agarose with 0.1% CTAB, 125 mM tricine-NaOH (pH 10.0). Agarose stacking gels were cast directly onto acrylamide gels and allowed to cool thoroughly before the comb was removed. Alternatively, low % T acrylamide stackers (polymerized with 0.1% ammonium persulfate and 0.025% TEMED were used. Running buffer was prepared as a 5X stock which contained 0.5% CTAB, 125 mM tricine brought to pH 8.2 using approximately 75 ml per liter of 1M arginine free base.

Several electrophoresis apparatus from different manufacturers were used interchangeably; gels presented here were run using either a BioRad MiniProtean II apparatus or Hoefer Sturdier Gel apparatus. Gels were run at the temperature indicated in the text until the salt/dye front approached the end of the gel (approximately 45 minutes for mini-gels and 4 hours for large gels) at 100 V through the stacking gel, and 150 V through the separating gel. Since CTAB/protein complexes were cationic, it was necessary to reverse the electrode connections to the power supply so that the proteins ran into the gel.

Example 4

Protein Staining

Gels were first fixed in 10% acetic acid/25% methanol for 15 minutes, then stained with 0.025% CBB in 25% isopropanol, 10% acetic acid for 1 hour. Gels were destained for 20 minutes in 0.001% CBB in 10% isopropanol, 10% acetic acid; destaining was completed with several changes of 10% acetic acid. When necessary, gels were subsequently silver stained by the method of Oakley et al., *Anal. Biochem.*, 105:361-363 (1980).

Example 5

Detection of Enzyme Activities

*Spectrophotometric Assays.* Peroxidase activity was assayed at room temperature using a solution of 0.5 mg/ml diaminobenzidine in 10 mM sodium phosphate buffered 0.9% saline (pH 7.2), containing 0.1% hydrogen peroxide. Reactions were allowed to proceed for 5 minutes, and then were stopped by the addition of 10 mM sodium sulfide to 100 μM. Absorbance at 480 nm was used to determine the degree of product formation.

$Ca^{2+}$-ATPase activity was assayed by the method of Tuan and Knowles, *J. Biol. Chem.*, 259:2754-2763 (1984), without further modification. Alkaline phosphatase, lactate dehydrogenase, and isocitrate dehydrogenase activities were measured using protocols supplied with their respective diagnostic kits.

*Gel Histochemical Assays.* $Ca^{2+}$-ATPase activity from the chick CAM was visualized by the method of Tuan and Knowles, *J. Biol. Chem.*, 259:2754-2763 (1984), without further modification. Peroxidase activity was assayed by the method of Akin et al., *Anal. Biochem.*, 145:170-176 (1985), with positive reactions being visualized as reddish brown staining bands.

What is claimed is:

1. A discontinuous gel electrophoresis system comprising a first and second electrode; a separation gel matrix located between the electrodes comprising polyacrylamide, agarose, or polyacrylamide and agarose gels; a stacking gel, located between the first electrode and said separation gel matrix; and a running buffer solution, comprising a zwitterion, a buffer, and a charged surfactant comprising cetyltrimethylammonium, tetradecyltrimethylammonium, decylsulphate, octylsulphate, or dodecylsulfonate, said buffer solution being in contact with the first electrode and said stacking gel and also in contact with the second electrode and said separating gel.

2. The system of claim 1 wherein said zwitterion is selected from the group consisting of arginine, lysine, and glycine.

3. The system of claim 1 wherein the running buffer solution comprises a buffer selected from the group consisting of Tricine, Hepes, MOPS, and Tris.

4. A method for performing a discontinuous gel electrophoresis, comprising:
   (a) providing an electrophoresis system having a first and second electrode; a separation gel matrix, located between the first and second electrodes, comprising polyacrylamide, agarose, or polyacrylamide and agarose gels; a stacking gel, located between the first electrode and said separation gel matrix; and a running buffer solution, comprising a zwitterion, a buffer, and a charged surfactant comprising cetyltrimethylammonium, tetradecyltrimethylammonium, decylsulphate, octylsulphate, or dodecylsulfonate, said buffer solution being in contact with the first electrode and said stacking gel and also in contact with the second electrode and separating gel;
   (b) placing a protein-containing sample which has been solubilized with said surfactant in fluid contact with said stacking gel;
   (c) applying an electric current to the electrodes; and
   (d) separating the proteins contained in the sample.

5. The method of claim 4 wherein said zwitterion is selected from the group consisting of arginine, lysine, and glycine.

6. The method of claim 4 wherein said buffer solution comprises Tricine, Hepes, MOPS, or Tris.

7. The method of claim 4 wherein the surfactant is cetyltrimethylammonium bromide, the zwitterion is arginine, and the buffer comprises Tricine.

8. The system of claim 1 wherein the surfactant is cetyltrimethylammonium bromide, the zwitterion is arginine, and the buffer comprises Tricine.

* * * * *